United States Patent
Huber et al.

(10) Patent No.: US 7,011,626 B2
(45) Date of Patent: Mar. 14, 2006

(54) OPTICAL INSTRUMENT, IN PARTICULAR AN ENDOSCOPIC INSTRUMENT

(75) Inventors: Matthias Huber, Emmingen (DE);
Ulrich Kehr, Tuttlingen (DE)

(73) Assignee: Karl Storz GmbH & Co. KG, (DE)

( * ) Notice: Subject to any disclaimer, the term of this patent is extended or adjusted under 35 U.S.C. 154(b) by 0 days.

(21) Appl. No.: 10/664,279

(22) Filed: Sep. 17, 2003

(65) Prior Publication Data
US 2004/0127768 A1 Jul. 1, 2004

Related U.S. Application Data

(63) Continuation of application No. PCT/EP02/02601, filed on Mar. 9, 2002.

(51) Int. Cl.
*A61B 1/04* (2006.01)

(52) U.S. Cl. ........................... 600/133; 600/162

(58) Field of Classification Search ............... 600/101, 600/103, 133, 160–165, 169
See application file for complete search history.

(56) References Cited

U.S. PATENT DOCUMENTS

| | | | | |
|---|---|---|---|---|
| 4,779,613 A | * | 10/1988 | Hashiguchi et al. | 600/169 |
| 5,124,129 A | * | 6/1992 | Riccitelli et al. | 422/56 |
| 6,077,220 A | | 6/2000 | Rudischhauser et al. | 600/162 |

FOREIGN PATENT DOCUMENTS

| DE | 37 08 124 C2 | 8/1994 |
|---|---|---|
| DE | 195 07 205 A1 | 11/1995 |
| DE | 199 13 761 A1 | 9/2000 |

* cited by examiner

*Primary Examiner*—Beverly M. Flanagan
(74) *Attorney, Agent, or Firm*—St. Onge Steward Johnston & Reens LLC

(57) ABSTRACT

The invention relates to an optical instrument, in particular an endoscopic instrument, with a housing, containing at least one optical system and a hygroscopic substance, and in which an eyepiece is detachably secured to the housing. In order to design an optical instrument of the aforementioned type in such a way that the hygroscopic substance can be integrated easily and safely into the housing, the invention proposes that the hygroscopic substance should be imbedded in a moldable matrix material and that the matrix material caulked with the hygroscopic substance can be replaceably inserted in the eyepiece.

10 Claims, 2 Drawing Sheets

OPTICAL INSTRUMENT, IN PARTICULAR AN ENDOSCOPIC INSTRUMENT

This application is a continuation of pending International Patent Application No. PCT/EP02/02601 filed on Mar. 9, 2002 which designates the United States and claims priority of pending German Application No. 101 13 365.0 filed on Mar. 20, 2001.

FIELD OF THE INVENTION

The invention relates to an optical instrument, in particular an endoscopic instrument, with housing containing at least one optical system and a hygroscopic substance, and in which an eyepiece is detachably secured to the housing.

Optical instruments, and in particular those employed in medical technology such as endoscopic instruments, are primarily fluid-tight systems. For a number of reasons, however, it is possible for humidity to penetrate the housing, which can result in a clouding of the optical systems that worsens the visibility. Problems can arise, for instance, as early as the manufacturing stage of the instruments in normal atmosphere, if the moisture residue from the atmospheric air is precipitated in the housing interior. Moreover, as a result of slight leaks, moisture can penetrate at connecting points where the instrument can be dismantled for purposes of maintenance, repair, or insertion. Cleaning by means of autoclaving, in which the instrument is exposed at variable pressure to steam at about 140 degrees C., represents another severe risk. This temperature impact can result in fine fissures, another opportunity for dampness to penetrate the housing.

To avoid such dampness problems from moisture condensation on the optical system, it is a known procedure with optical instruments to install a hygroscopic substance in the housing, which substance retains the moisture forming inside the housing before this moisture is precipitated onto the at least one optical system.

Thus it is known, for instance, to insert the hygroscopic substance in loose form in the housing. The disadvantage here, however, is that upon moving the instrument, noises occur and in addition the motion causes abrasion of the hygroscopic substance, which can result in dust on the optical systems.

An endoscope is known from DE 37 08 124 C2 in which the hygroscopic substance is configured as a flexible strip material and is inserted in a part of the endoscope lens especially provided for the purpose, between the lens holder and the housing wall. This known configuration has the disadvantage that the endoscopic strip material can be replaced can be replaced only by completely disassembling the endoscope, which as a rule is done only in the manufacturing plant. The hygroscopic substance in this instrument, therefore, can be replaced only at considerable cost and time.

Patent DE 199 13 761 A1 reveals a dry device in which a drying material (hygroscopic substance) is imbedded in a moldable flat-shaped matrix material.

In DE 195 07 205 A1 it is proposed to install the hygroscopic substance under a wall section of the housing that can be disassembled, which section is connected by a coupling gas-tight with the remainder of the housing wall. This embodiment allows a rapid, simple exchange of the hygroscopic substance, but only if one accepts the disadvantage that the endoscope has an additional aperture, whose fluid-tightness must be assured.

Consequently, it is the aim of the invention to design an optical instrument of the aforementioned type in such a way that the hygroscopic substance can be integrated easily and safely in the housing.

This aim is fulfilled through the invention in that the hygroscopic substance is imbedded in a moldable matrix material and in that the matrix material caulked with the hygroscopic substance can be replaceably inserted in the eyepiece.

As a result of the inventive imbedding of the hygroscopic substance into a freely moldable matrix material, which can be replaceably inserted in the eyepiece, it becomes possible for the first time to arrange the hygroscopic substance securely, resistant to moving and abrasion, in such a way that the hygroscopic substance is inserted so that it can be replaced in the housing easily and quickly. Because the substance is a component of the portion of the structure shaped by the matrix material, there is no need for separate installation with additional securing elements, as is customary in the state of the art.

In order to reinforce the moisture absorption by the imbedded hygroscopic substance on the one hand, and on the other hand to ensure free shapability to any desired geometric shape, it is proposed that the matrix material should be elastic and penetrable to moisture when hardened. Elastomers on a silicon and/or polyurethane base, for instance, can be used as inventive matrix materials having these properties and moreover capable of being produced by injection molding.

Through injection molding or other shaping methods, for instance, it is therefore possible to configure the matrix material caulked with the hygroscopic substance as a cylindrical sheath that can be placed in the eyepiece of the optical instrument or as an O-ring that can be placed in the housing of the optical instrument.

According to an advantageous embodiment of the invention, it is further proposed that the moisture coating of the hygroscopic substance should be optically recognizable, for instance through different coloring of the substance. Use of a hygroscopic substance with such an indicator property is particularly advantageous because the user of the instrument can verify the condition of the hygroscopic substance, for instance through a control window, in order to replace this substance as necessary along with the shaping matrix material.

Silica gel or porous ceramics, so-called molecular sieves, can be used as materials for the hygroscopic substance.

It is finally proposed with the invention that the hygroscopic substance should consist of a mixture of various hygroscopic substances. In his manner the various properties of the substances can be combined as necessary in order to receive the best possible substance for the particular application purpose Additional properties and advantages of the invention are presented in the following description of the attached drawing, in which two embodiments of an inventive optical instrument are set forth merely as examples and in schematic form. The illustrations are as follows:

DETAILED DESCRIPTION OF THE DRAWINGS

Figure 1:
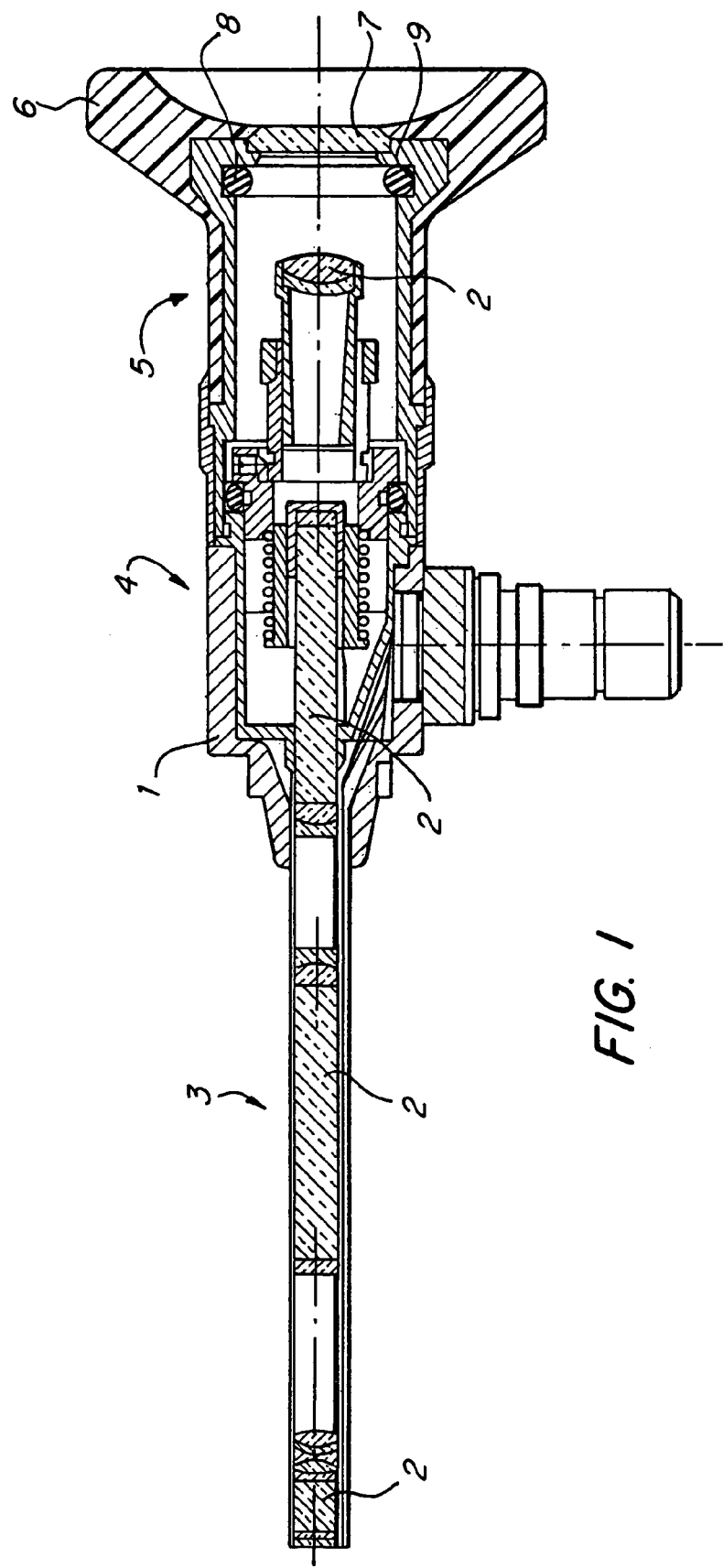
FIG. 1 Longitudinal section through a first embodiment of an inventive optical instrument FIG. 2 Longitudinal section through a second embodiment of an inventive optical instrument
Figure 2:
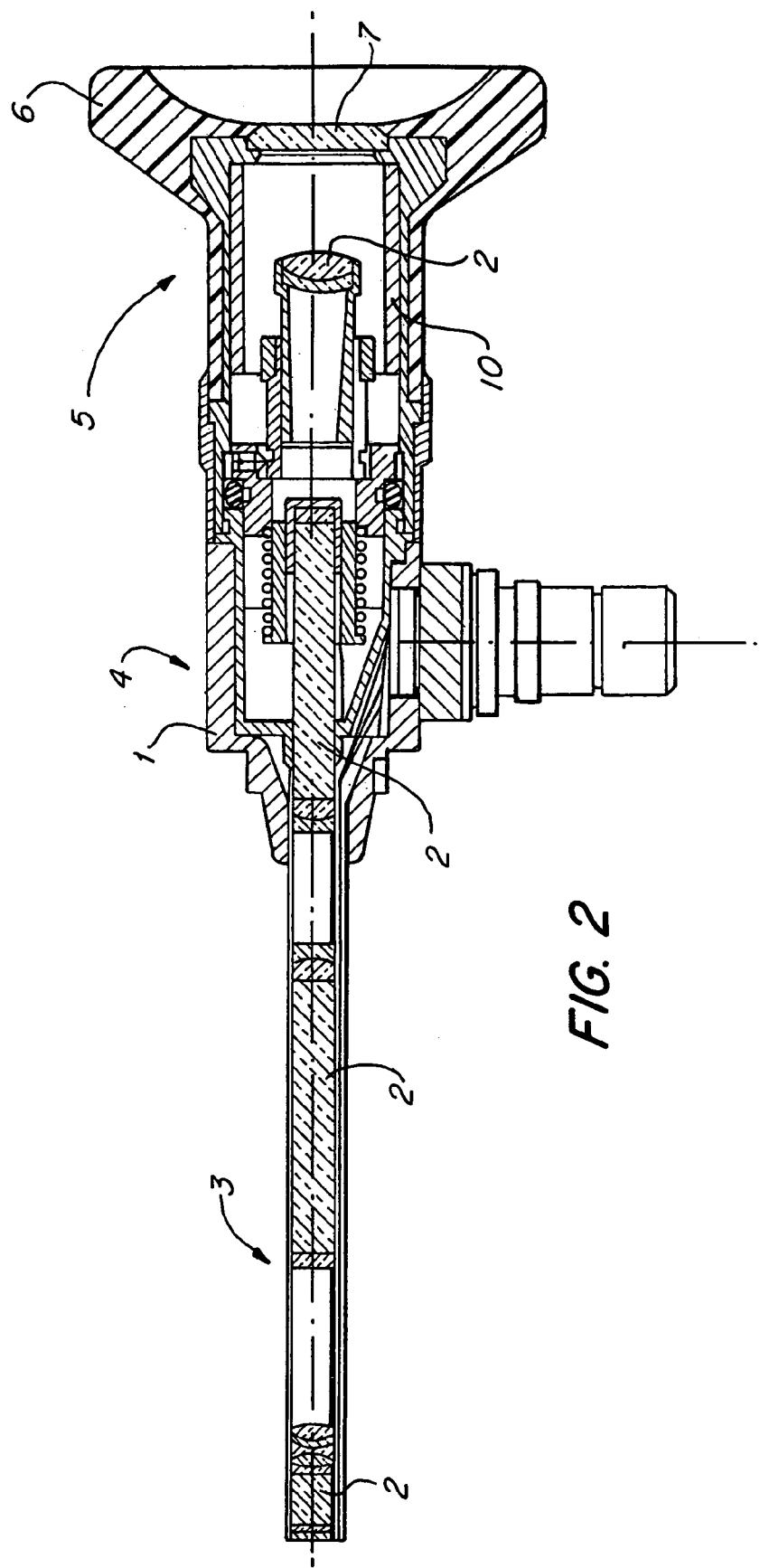

In the optical instrument illustrated in FIGS. 1 and 2 we see a rigid endoscope with a housing 1 for receiving optical systems 2, in this case a lens system.

The housing 1 consists of a thin shaft 3 on the distal side and a handle part 4 of greater diameter on the proximal side. Inside the handle part 4 connected fluid-tight with the shaft 3, an ocular unit 4 is installed. To observe the image transmitted by means of the optical system 2 to the ocular unit 5, on the proximal end of the handle part 4 an eyepiece 6 is mounted through which the user of the endoscope can observe the image without risk of glare or interfering light. The eyepiece 6 on the one hand is screwed together with the housing 1 and on the other hand by means of an ocular cover glass 7 fluid-tight, for instance cemented on.

To remove any residual dampness in the housing and to absorb moisture penetrating the housing 1 through leaks, a hygroscopic substance such as silica gel is installed in the housing.

In the two embodiments of an endoscope illustrated in FIGS. 1 and 2, the hygroscopic substance is imbedded in a moldable matrix material and, as a consequently shaped component, is integrated into the housing 1 of the endoscope. The matrix material, shapable for instance by injection molding and caulked with the hygroscopic substance, is configured in the first embodiment, shown in FIG. 1, as an O-ring which can be secured inside a surrounding ring groove 9.

According to the second embodiment as shown in FIG. 2, the moldable matrix material is configured as a cylindrical sheath 10 inserted in the housing 1.

By imbedding the hygroscopic substance into the moldable matrix material, it is possible to insert the hygroscopic material in the housing where desired and in a great variety of shapes, without the necessity of using special installation elements for the purpose. The matrix material, resistant to abrasion and to moving and easy to place and containing the hygroscopic substance, can moreover be quickly and easily replaced.

In the illustrated embodiments it is necessary only to unscrew the eyepiece 6 from the handle 4 of the housing 1 in order to remove the O-ring 8 or the sheath 10 and replace them with a new, dry component. By using a hygroscopic substance that reveals the moisture coating by a different color, the use of the instrument can be made still easier because the coating of the hygroscopic substance with moisture can be detected externally, for instance by a special view window (not illustrated) or by means of an ocular cover glass 7.

In a practical attempt to produce an O-ring 8 according to FIG. 1, 2K-additive enlacing silicon was used as a material for the matrix basic material and silica gel (blue) was used as hygroscopic substance.

FIGURE KEY 1 housing
2 optical system
3 shaft
4 handle part
5 ocular unit
6 eyepiece
7 ocular cover glass
8 O-ring
9 ring groove
10 sheath

What is claimed is:

1. Optical instrument, in particular an endoscopic instrument comprising, a housing in which at least one optical system and a replaceable hygroscopic substance are inserted, and in which an eyepiece is detachably secured to the housing wherein the hygroscopic substance is imbedded in a moldable matrix material and the matrix material caulked with the hygroscopic substance is inserted replaceably in the eyepiece.

2. Optical instrument according to claim 1, wherein the matrix material caulked with the hygroscopic substance is configured as an O-ring that can be inserted into the eyepiece.

3. Optical instrument according to claim 1, wherein the matrix material caulked with the hygroscopic substance is configured as a cylindrical sheath that can be inserted into the eyepiece.

4. Optical instrument according to claim 3, wherein the moldable matrix material is elastic and penetrable to moisture when hardened.

5. Optical instrument according to claim 4, wherein the moldable matrix material is an elastomer on a silicon and/or polyurethane base.

6. Optical instrument according to claim 5, wherein the matrix material caulked with the hygroscopic substance can be produced by injection molding.

7. Optical instrument according to claim 5, wherein the moisture coating of the hygroscopic substance can be optically identified.

8. instrument according to claim 7, wherein the hygroscopic substance indicates the moisture coating by a difference in color.

9. Optical instrument according to claim 8, wherein the hygroscopic substance is a silica gel or a porous ceramic.

10. Optical instrument according to claim 8, wherein the hygroscopic substance consists of a mixture of various hygroscopic substances.

* * * * *